(12) United States Patent
Brocco

(10) Patent No.: US 9,365,886 B2
(45) Date of Patent: Jun. 14, 2016

(54) DEVICE FOR STANDARDISING THE IN-VITRO SYNERGY TESTING OF TWO ANTIBIOTICS THROUGH THE METHOD CROSSING THE GRADIENT STRIPS

(71) Applicant: Silvio Brocco, Roseto Degli Abruzzi (IT)

(72) Inventor: Silvio Brocco, Roseto Degli Abruzzi (IT)

(73) Assignee: LIOFILCHEM S.R.L., Roseto Degli Abruzzi (TE) (IT)

( * ) Notice: Subject to any disclaimer, the term of this patent is extended or adjusted under 35 U.S.C. 154(b) by 0 days.

(21) Appl. No.: 14/404,849

(22) PCT Filed: Jun. 6, 2013

(86) PCT No.: PCT/EP2013/001667
§ 371 (c)(1),
(2) Date: Dec. 1, 2014

(87) PCT Pub. No.: WO2013/185896
PCT Pub. Date: Dec. 19, 2013

(65) Prior Publication Data
US 2015/0152465 A1 Jun. 4, 2015

(30) Foreign Application Priority Data
Jun. 11, 2012 (IT) .............................. AN2012A0069

(51) Int. Cl.
*C12Q 1/20* (2006.01)
*C12Q 1/18* (2006.01)
*C12M 1/22* (2006.01)
*C12M 1/00* (2006.01)

(52) U.S. Cl.
CPC ................. *C12Q 1/20* (2013.01); *C12M 23/10* (2013.01); *C12M 23/34* (2013.01); *C12Q 1/18* (2013.01)

(58) Field of Classification Search
CPC ........ C12M 23/10; C12M 23/34; C12Q 1/18; C12Q 1/20; B01L 2300/0825; B01L 2300/0829
USPC ........................................................ 435/305.1
See application file for complete search history.

(56) References Cited

U.S. PATENT DOCUMENTS 5,344,761 A 9/1994 Citri
2012/0184906 A1* 7/2012 McAllister ........ A61M 37/0015
604/136

OTHER PUBLICATIONS

International Search Report for corresponding International Application No. PCT/EP2013/001667.
H. Sueke et al: "An In Vitro Investigation of Synergy or Antagonism between Antimicrobial Combinations against Isolates from Bacterial Keratitis", Investigative Ophthalmology & Visual Science, vol. 51, No. 8, Aug. 1, 2010, pp. 4151-4155.
White: "Comparison of three different in vitro methods of detecting synergy: time-kill, checkerboard, and E test.", Antimicrobial Agents and Chemotherapy, vol. 40, No. 8, Jan. 1, 1996, p. 1914.

* cited by examiner

*Primary Examiner* — Nathan Bowers
*Assistant Examiner* — Lydia Edwards
(74) *Attorney, Agent, or Firm* — Egbert Law Offices, PLLC

(57) ABSTRACT

A device for microbiological analyzes is provided. More specifically, a device is provided for standardizing the crossing and allowing a perfect angle of 90° between two graduated paper strips impregnated with a predefined concentration gradient of an antimicrobial agent, for evaluating their synergistic effect on the minimum inhibitory concentration (MIC) on a bacterial culture medium.

5 Claims, 2 Drawing Sheets

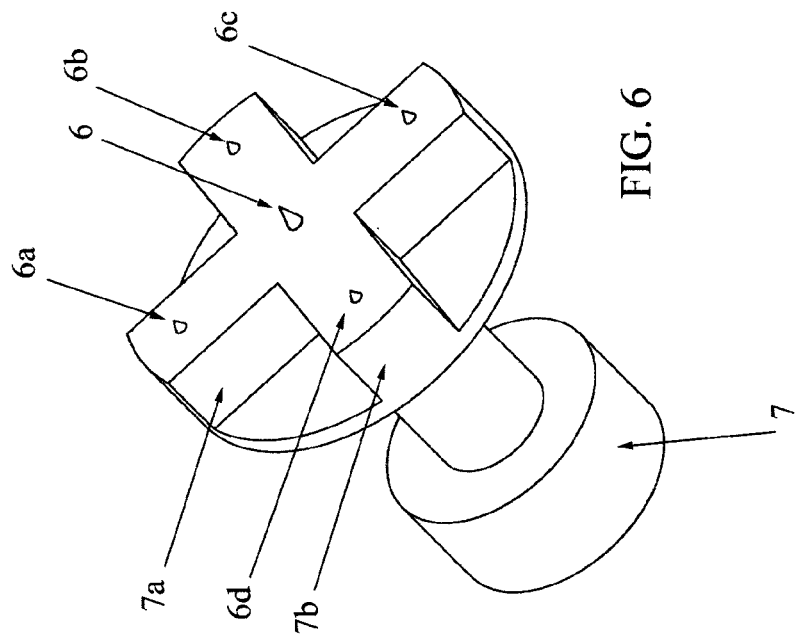
FIG. 6
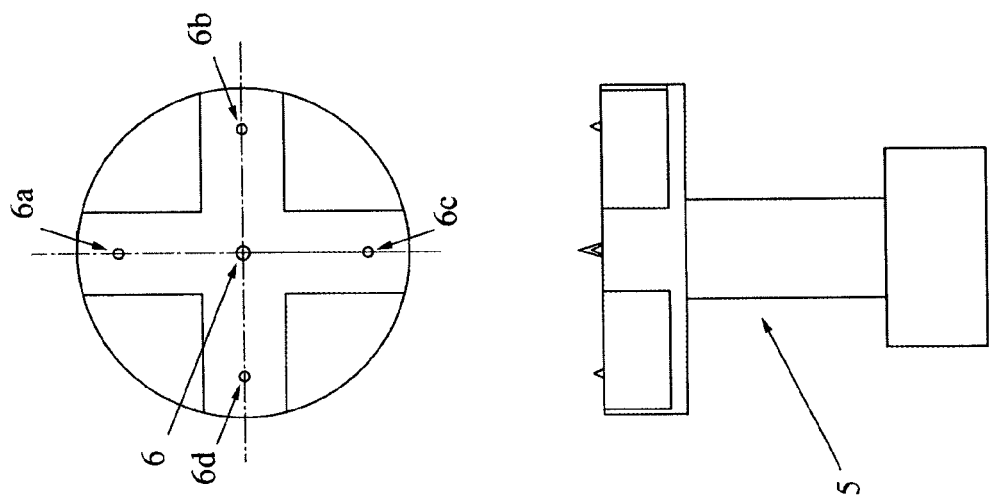
FIG. 4
FIG. 5

DEVICE FOR STANDARDISING THE IN-VITRO SYNERGY TESTING OF TWO ANTIBIOTICS THROUGH THE METHOD CROSSING THE GRADIENT STRIPS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention concerns the sector of microbiological analyses.

2. Description of Related Art Including Information Disclosed Under 37 CFR 1.97 and 37 CFR 1.98.

In medicine, in order to combat a resistant germ, it is often necessary to administer one or two antibiotics to a patient at the same time, for which reason it is firstly essential to perform a synergy test in order to verify their compatibility and their associated effect.

The synergy test of two antibiotics performed on a bacterial culture medium is, in fact, essential for the purpose of verifying:

an antagonistic effect of the two antibiotics to be administered to the patient, in the sense that the two antibiotic molecules combined together produce a lesser effect than they would produce if considered individually;—a synergistic effect of the two antibiotics to be administered to the patient, in the sense that the two antibiotic molecules combined together produce a greater effect than the sum of the single effects of the two molecules;

an additive effect of the two antibiotics to be administered to the patient, in the sense that the two antibiotic molecules combined together produce an effect that it is equal to the sum of the single effects of the two molecules;

an indifferent effect of the two antibiotics to be administered to the patient which occurs when the two antibiotic molecules, even if combined together, do not produce an improved effect compared to what they would have produced if considered individually.

At the present state of the art, there are different methods for testing for synergy between antibiotic molecules: time-kill in broth macrodilution[1], checkerboard in broth microdilution[2], substitution of the antimicrobial gradient strips on microbial culture through agar diffusion[1], crossing of antimicrobial gradient strips on microbial culture through agar diffusion[4].

[1, 2, 4] *Comparison of three different in-vitro methods of detecting synergy: time-kill, checkerboard, and Etest.* R L White, D S Burgess, M Manduru and J A Bosso Antimicrob. Agents Chemother. 1996, 40(8): 1914.

[1, 2, 3] *Comparison of Etest, chequerboard dilution and time-kill studies for the detection of synergy or antagonism between antifungal agents tested against Candida species.* Lewis, R., Diekema, D., Messer, S., Pfaller, M. and Klepser, M. (2002). JAC. 49: 345-351.

The determination of the minimum inhibitory concentration (MIC) of an antimicrobial agent against a microorganism through the use of graduated strips impregnated with antimicrobial gradient consists of depositing a strip, made of a porous or non porous material on a microbial population on an agar culture medium. The antibiotic strip releases the antibiotic according to the predefined gradient, and after an incubation period of 18 hours or more, an elliptical inhibition area, symmetrical and centred along the strip, can be observed.

The MIC value, expressed in µg/mL, is read at the intersection point between the lower edge of the inhibition ellipse and the strip.

The synergy test of two antimicrobial agents through the use of the gradient strip with the crossing method of the strips on microbial culture medium firstly involves the determination of the MIC for each antibiotic; then, the strips of the two antibiotics are placed perpendicularly on the bacterial culture. The two strips must cross at the point corresponding to the MIC values of the two individual antimicrobial agents previously determined. After incubation, the new MIC of each antibiotic is evaluated and the combined effect of the same is calculated using the following algorithm[5, 6]:

Defined:
$MIC_A$=MIC of antibiotic A
$MIC_B$=MIC of antibiotic B
$MIC_{AB}$=MIC of antibiotic A in presence of antibiotic B;
$MIC_{BA}$=MIC of antibiotic B in presence of antibiotic A.

The FIC (Fractional Inhibitory Concentration index) is calculated:

$$\text{FIC index} = MIC_{AB}/MIC_A + MIC_{BA}/MIC_B$$

| | |
|---|---|
| Synergy | FIC <0.5 |
| Additivity | FIC >0.5 and <1.0 |
| Indifference | FIC >1 and <4 |
| Antagonism | FIC >4 |

[5] *Comparison of techniques for measurement of in vitro antibiotic synergism.* Norden, C. W., Wentzel, H., Keleti, E. *J. Infect. Dis.* 140:629-633, 1979.

[6] *Correlations between methods for measurement of synergy.* Berenbaum, M. C. 1980. J. Infect. Dis. 142:476-480.

The accuracy of this synergy test method depends on the correct crossing of the two antimicrobial gradient strips which must be perfectly perpendicular. The performance of this test is susceptible to errors by the operator, who could accidentally fail to position the strips at an angle of 90° or fail to pinpoint the correct crossing point during manual depositing of the second strip on top of the first, which would result in a test to be repeated or in obtaining unreliable results.

The intersection of the strips at 90° is the condition required for the correct evaluation of the inhibition rings and the reading of the value of the MIC on the graduated strip and the consequent calculation of the above-described algorithm.

The depositing of the second strip at the desired crossing point is difficult and susceptible to error because it is common practice in laboratories to perform this operation manually by lab forceps, attempting to achieve a millimetric positioning on the exact point of the graduated strip that corresponds to the MIC point, exposing the operator to natural imprecision. Once the antimicrobial strip has come into contact with the bacterial culture it can no longer be removed nor repositioned inasmuch as the process of diffusion of the antibiotic is immediate when it comes into contact with the agar.

BRIEF SUMMARY OF THE INVENTION

The object of the present invention is to remedy the aforementioned problems by offering a device to the microbiologists or lab technicians, by allowing the crossing of two graduated paper strips impregnated with two different antibiotics perfectly at 90°, thus facilitating the execution of the synergy testing of antibiotics on a bacterial culture medium.

Another object of the present invention is to render the synergy test accurate by ensuring the exact crossing at 90° of two graduated paper strips, impregnated with two different antibiotics.

Another object of the present invention is to standardise the synergy testing method in order to guarantee intra-laboratory repeatability to the said synergy tests and inter-laboratory reproducibility.

These and other objects are achieved by the invention that is the subject of the present application that concerns a device that makes it possible to cross perfectly at an angle of 90° two graduated paper strips each of which is impregnated with a predefined concentration gradient of an antimicrobial agent for determining the exact outcome of their synergistic effect.

BRIEF DESCRIPTION OF THE DRAWINGS

Further features and advantages of the invention shall be better understood from the description of a preferred but not exclusive embodiment of the same, illustrated by way of indicative but non-limiting example in the accompanying drawings in which.

a circular hollow (3) with a diameter of 20 mm;
a circular hollow (4) with a diameter of 4 mm concentric to the circular hollow (3);
four circular hollows (4a, 4b, 4c, 4d) with a diameter of 2 mm and a depth of 1.5 mm positioned at a distance of 7.5 mm from the centre of the circular hollow (4).

Figure 2:
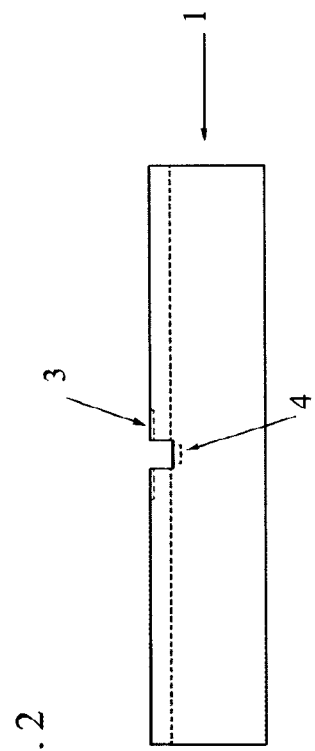

FIG. 2 is a side view of the circular base (1) with a width of 20 mm, of the circular hollow (3) with a depth of 0.7 mm and of the circular hollow (4) with a depth of 5.4 mm.

Figure 3:
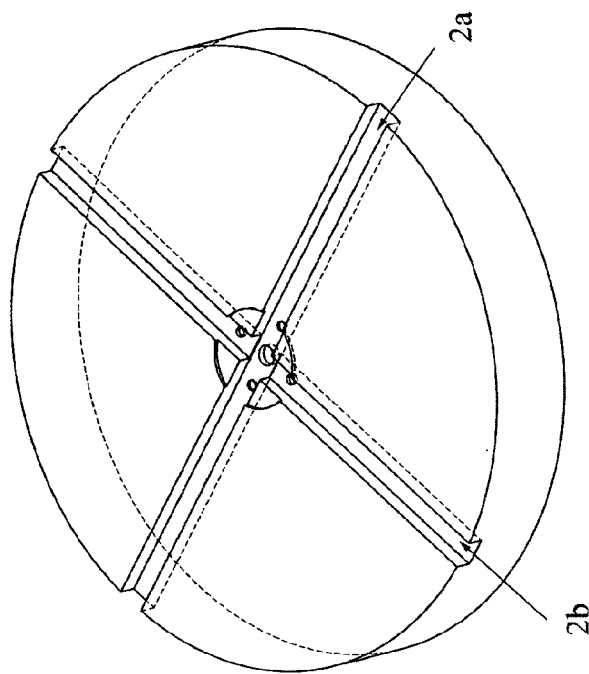
Figure 1:
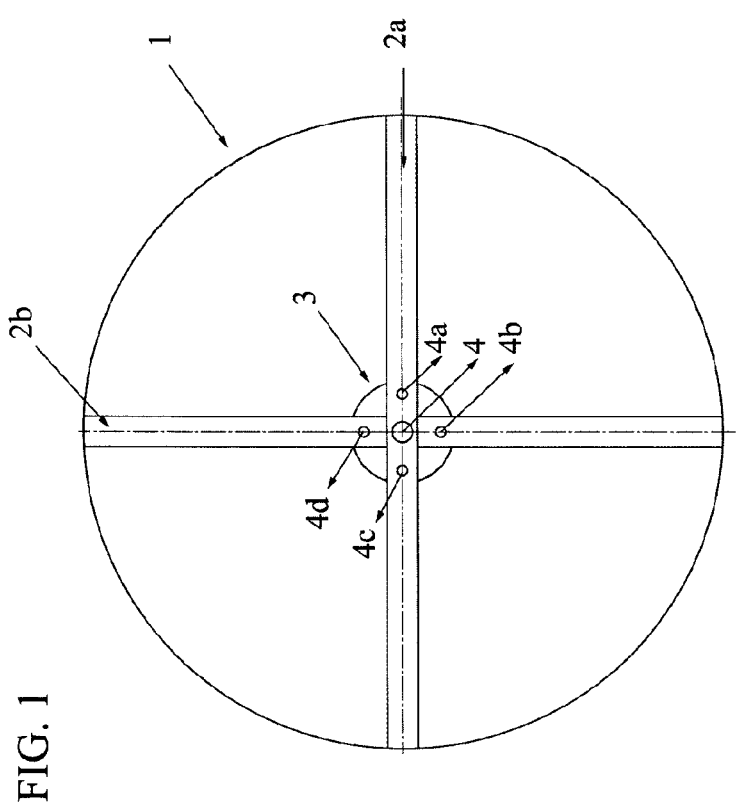
FIG. 1 shows a view from above of a circular base (1) with a diameter of 124 mm comprising two grooves (2a, 2b) which cross perfectly at 90°, staggered in height and each having a width of 6 mm which corresponds to the width of the strip of graduated paper (not shown), on which the aforementioned graduated strips are made to slide each one independently of the other. At the centre of the circular base (1) there is.

FIG. 3 is an axonometric view of the circular base (1) clearly displaying the two grooves (2a, 2b) staggered in height, created in order to allow the two graduated paper strips to slide independently.

FIG. 4 is a view from above of a disposable crossed piercing picker (5) in which the following features are highlighted: a central needle/point (6) with a diameter of 8 mm and a height of 1.4 mm and four needles/points (6a, 6b, 6c, 6d) with a diameter of 6 mm and a height of 0.4 mm, positioned at a distance of 7.5 mm from the centre of the needle/point (6).

FIG. 5 is a side view of the disposable crossed piercing picker (5) with a diameter of 20 mm, equipped with a needle/point (6) at the centre which serves, once inserted into the appropriate circular hollow (3), to pierce and pick up the graduated paper strips perfectly crossed at an angle of 90°, and equipped with four additional needles/points (6a, 6b, 6c, 6d) which serve to prevent the strips from rotating during the transfer from the circular base (1) to the bacterial culture on the Petri dish.

FIG. 6 is an axonometric view of the disposable crossed piercing picker (5) clearly displaying two crossed blocks (7a, 7b) able to fit compatibly into the grooves (2a, 2b) staggered in height on the circular base (1), at the centre of which there is a needle/point (6) and, at a distance of 7.5 mm from the centre of the needle/point (6) there are four needles/points (6a, 6b, 6c, 6d), and a knob (7) with a diameter of 12 mm.

DETAILED DESCRIPTION OF THE INVENTION

The invention that is the object of the present application concerns a device consisting of a circular base (1) which serves for crossing two graduated strips of paper and a disposable crossed piercing picker (5) which serves to pick up and transfer the two graduated paper strips, each of which has been previously impregnated with a predefined concentration gradient of an antimicrobial agent, from the circular base (1) 20 mm high in order to cross them perfectly at an angle of 90° at the points obtained as a result of the respective MICs performed earlier, with a view to determining an exact synergistic evaluation, once they have been placed on a bacterial culture medium.

The surface of this circular base (1) with a diameter of 124 mm presents two grooves (2a, 2b) crossed at an angle of 90° having a rectangular section 6 mm wide and staggered in height.

The first groove (2a) along which the first graduated paper strip (not shown) will be made to slide is 3.9 mm deep, while the second groove (2b) along which the second graduated strip of paper (not shown) will be made to slide, independently of the first, is 3.6 mm deep.

This staggered effect between the two crossed grooves (2a, 2b) corresponds exactly to the thickness of one of the two graduated paper strips and it is for this very reason that the strips, once fitted in their respective crossed grooves (2a, 2b), can slide independently of one another inasmuch as one slides on top of the other, in such a way that the two strips cross each other exactly at the graduated points corresponding to their minimum inhibitory concentration values (MIC), obtained earlier.

On the upper surface of this circular base (1) there is a circular hollow (3) 0.7 mm deep which serves to facilitate the centring of the disposable crossed piercing picker (5) thanks to its two crossed blocks (7a, 7b) which fit compatibly into the grooves (2a, 2b) in the circular base (1); this disposable crossed piercing picker (5) has a needle/point (6) at the centre with a diameter of 8 mm and a height of 1.4 mm which serves to pierce and pick up the two graduated paper strips from the circular base (1) and place them on the bacterial culture medium on the Petri dish.

In order to facilitate the picking up of the two graduated paper strips, the fitting of a further four needles/points (6a, 6b, 6c, 6d) with a diameter of 6 mm and a height of 0.4 mm is provided for, the said points being positioned at an equal distance of 7.5 mm from the centre of the needle/point (6), for the purpose of preventing the possible rotation of the strips around the needle during transfer.

Concentric to the circular hollow (3) of the circular base (1) is the circular hollow (4), which has a diameter of 4 mm and a depth of 5.4 mm, the purpose of which is to facilitate the sinking of the needle of the disposable crossed piercing picker (5) into the two graduated paper strips, in such a way as to pick them up from the circular base (1) and place them on the bacterial culture agar crossed exactly at an angle of 90°. At an equal distance of 7.5 mm from the centre of the circular hollow (4) of the circular base (1), there are four circular hollows (4a, 4b, 4c, 4d), that have a diameter of 2 mm and a depth of 1.5 mm, the purpose of which, as above, is to facilitate the sinking of the needles/points (6a, 6b, 6c, 6d) of the disposable crossed piercing picker (5) into the two graduated paper strips. The humidity of the bacterial culture agar will facilitate the detaching of the two strips from the disposable crossed piercing picker (5) without the risk of their position at 90° undergoing variations.

Once the aforementioned strips release the antibiotic onto the bacterial culture agar, an ellipse is formed; after this, on the basis of the results of the MICs obtained from the combination of the two graduated strips, the effect of the two antibiotics combined will be evaluated: synergistic effect, antagonism, indifference or additive effect.

The materials and the dimensions of the above-described invention, illustrated in the accompanying drawings and later claimed, may be varied according to requirements. Moreover, all the details may be replaced by other technically equivalent ones without, for this reason straying from the protective scope of the present invention patent application.

The invention claimed is:

1. A device for standardizing in-vitro synergy testing of two antibiotics by a crossing method, the device comprising:
   a circular base adapted to receive two graduated paper strips such that the two graduated paper strips cross each other, the two graduated paper strips each being impregnated with a predefined concentration gradient of an antimicrobial, said circular base having a pair of grooves formed into an upper surface thereof, said pair of grooves adapted to receive respectively said two graduated paper strips, said pair of grooves crossing each other at an angle of 90°; and
   a disposable cross piercing picker which has a pair of crossed blocks that fit keep in compatibly in said pair of grooves, said disposable cross piercing picker having a first needlepoint disposed on a center thereof on surface of said pair of crossed blocks at a crossing of said pair of crossed blocks, said disposable crossed piercing picker having second and third needlepoints disposed on the surface of said pair of crossed blocks on opposite sides of and at equal distances from said first needlepoint, said disposable crossed piercing picker having fourth and fifth needlepoints disposed on the surface of another of said pair of crossed blocks on opposite sides of and at equal distances from said first needlepoint, the needlepoints being adapted to lift the two graduated paper strips from said pair of grooves.

2. The device of claim 1, each of said pair of grooves having a rectangular section having a width of 6 millimeters, said one of said pair of grooves having a depth of 3.9 millimeters, another of said pair of grooves having a depth of 3.6 millimeters.

3. The device of claim 1, said upper surface of said circular base having a first circular hollow formed therein, said first circular hollow having a diameter of 20 millimeters and a depth of 0.7 millimeters.

4. The device of claim 3, said circular base having a second circular hollow formed therein, said second circular hollow being concentric to said first circular hollow, said second circular hollow having a diameter of 4 millimeters and a depth of 5.4 millimeters.

5. The device of claim 4, one of said pair of grooves having a first pair of circular hollows each on opposite sides of said second circular hollow and located at a distance of 7.5 millimeters from a center of said second circular hollow, another of said pair of grooves having a second pair of circular hollow each on opposite sides of said second circular hollow and located at a distance of 7.5 millimeters from the center of said second circular hollow, each of the circular hollows in said pair of grooves having a diameter of 2 millimeters and a depth of 1.5 millimeters.

\* \* \* \* \*